US012583806B2

(12) United States Patent     (10) Patent No.:   US 12,583,806 B2

Gee et al.     (45) Date of Patent:    Mar. 24, 2026

(54) ALKYL ALUMINUM CATALYST DEACTIVATION WITH WATER AND SOLIDS REMOVAL VIA FILTRATION

(71) Applicant: Chevron Phillips Chemical Company LP, The Woodlands, TX (US)

(72) Inventors: Jeffrey C. Gee, Kingwood, TX (US); Brooke L. Small, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 258 days.

(21) Appl. No.: 18/475,779

(22) Filed: Sep. 27, 2023

(65) Prior Publication Data

US 2025/0100952 A1     Mar. 27, 2025

(51) Int. Cl.
    *C07C 2/30*       (2006.01)
    *B01J 31/12*      (2006.01)
    *B01J 31/14*      (2006.01)

(52) U.S. Cl.
    CPC .............. *C07C 2/30* (2013.01); *B01J 31/122* (2013.01); *B01J 31/143* (2013.01); *B01J 2231/20* (2013.01); *B01J 2531/31* (2013.01); *C07C 2531/14* (2013.01)

(58) Field of Classification Search
    CPC ...... C07C 2/30; C07C 2531/14; B01J 31/122; B01J 31/143; B01J 2231/20; B01J 2531/31
    USPC .......................................................... 585/522
    See application file for complete search history.

(56) References Cited

U.S. PATENT DOCUMENTS 10,112,876 B2 * 10/2018 Azam ........................ C07C 2/34
2014/0357919 A1 * 12/2014 Sadasivan Vijayakumari ............. B01J 38/12
585/653

FOREIGN PATENT DOCUMENTS

WO     WO-2013095720 A1 * 6/2013 ................ C08F 2/42

* cited by examiner

*Primary Examiner* — Prem C Singh
*Assistant Examiner* — Francis C Campanell
(74) *Attorney, Agent, or Firm* — Scheef & Stone, LLP

(57) ABSTRACT

Water is combined with an oligomer product that contains an oligomer and an alkyl aluminum catalyst to deactivate the catalyst and form a treated product containing the oligomer and aluminum-containing solids. The aluminum-containing solids then can be separated from the treated product.

18 Claims, 3 Drawing Sheets

ALKYL ALUMINUM CATALYST DEACTIVATION WITH WATER AND SOLIDS REMOVAL VIA FILTRATION

FIELD OF THE DISCLOSURE

The present disclosure generally relates to oligomerization processes, and more particularly to the deactivation of oligomerization catalysts and the purification of oligomerization products.

BACKGROUND

Feedstocks for the oligomerization reactions include olefin monomers that are contacted with a catalyst that must be deactivated (i.e., quenched) to stop the oligomerization reaction. One example of the catalyst used for oligomerization reactions is an alkyl aluminum catalyst that can be quenched with an aqueous alkaline solution. However, this type of quench creates an emulsion from which it is difficult to separate the oligomer product. The emulsion can also complicate removal of undesired substances from the desired oligomer product. Another drawback is that the quench produces large volumes of aqueous waste that have expensive disposal costs. The oligomerization reaction can also generate trace amounts (e.g., 0.5 wt % or less) of cross-linked polyethylene (PE) that is not easily removed from the product using standard filtration technologies.

The need remains for improved methods to quench oligomerization reaction catalysts. The need also remains for improved methods of removing undesired substances from oligomerization reaction products. Such improvements can result in lower production costs, improved product quality, and so forth.

SUMMARY

Disclosed is a process that includes combining water with an oligomer product including an oligomer and an alkyl aluminum catalyst to form a treated product including the oligomer and aluminum-containing solids; and separating, by a filter or filtration process, the treated product into a permeate stream including the oligomer and a retentate stream including the aluminum-containing solids.

Also disclosed herein is an alkyl aluminum catalyst deactivation system that can include an oligomerization reactor configured to contact an olefin monomer in a presence of an alkyl aluminum catalyst to form an oligomer product including an oligomer and the alkyl aluminum catalyst; a mixing vessel having a first inlet fluidly coupled to an outlet of the oligomerization reactor; a water stream fluidly coupled to the first inlet of the mixing vessel or to a second inlet of the mixing vessel, wherein the water stream includes water and is configured to combine the water with the oligomer product to deactivate the alkyl aluminum catalyst, wherein the water is combined with the oligomer product at a location that is i) upstream of the first inlet of the mixing vessel or ii) in the mixing vessel; and a separator having an inlet coupled to an outlet of the mixing vessel, wherein the separator includes a filter and is configured to filter a treated product received from the mixing vessel into a permeate stream and a retentate stream, wherein the treated product includes the oligomer and aluminum-containing solids, wherein the permeate stream includes the oligomer, wherein the retentate stream includes the aluminum-containing solids.

Other technical features may be readily apparent to one skilled in the art from the following figures, descriptions, and claims.

BRIEF DESCRIPTION OF THE DRAWINGS

For a more complete understanding of this disclosure, reference is now made to the following description, taken in conjunction with the accompanying drawings, in which.

DETAILED DESCRIPTION

Figure 1:
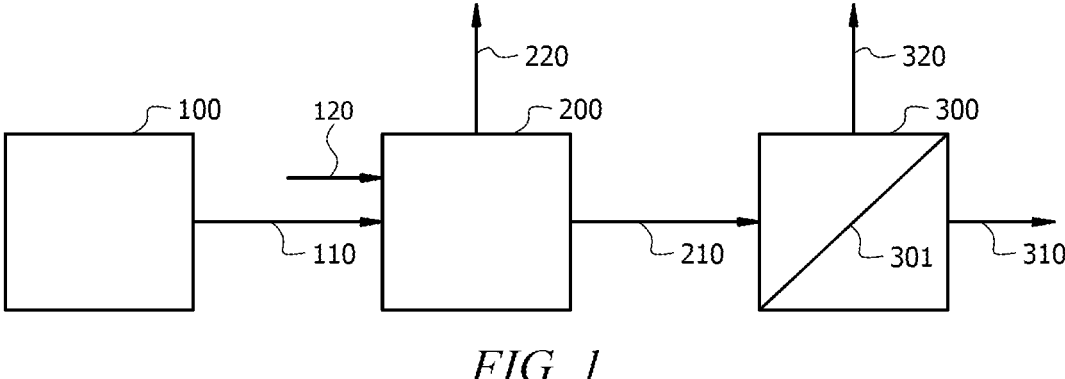
FIG. 1 is a schematic diagram of an alkyl aluminum catalyst deactivation system and process as described herein.

It is to be understood that the following disclosure describes aspects, features, structures, and/or functions of the disclosure. Exemplary components, arrangements, and configurations described below are provided merely as examples, and are not intended to limit the scope of the disclosure. Moreover, the exemplary components, arrangements, and configurations described below can be present in any flow-through, e.g., any element from one component, arrangement, or configuration can be used in any other component, arrangement, or configuration without departing from the scope of the disclosure.

Additionally, certain terms are used throughout the following description and claims to refer to particular components. As one skilled in the art will appreciate, the naming convention for the elements described herein is not intended to limit the scope of the claimed subject matter, unless otherwise specifically defined herein. Further, the naming convention used herein is not intended to distinguish between components that differ in name but not function.

The term "stream" as used herein refers to a composition in a gas phase, in a liquid phase, in a solid phase, or any combination of phases. The term "stream" can additionally refer to and imply associated equipment, such as conduit, line, and pipe that is used to move the composition from one location to another. Alternatively, the term "stream" refers only to the composition contained within the equipment.

The term "alpha olefin" as used in this specification and claims refers to an olefin that has a double bond between the first and second carbon atom of the longest contiguous chain of carbon atoms. The term "alpha olefin" includes linear and branched alpha olefins unless expressly stated otherwise. In the case of branched alpha olefins, a branch may be at the 2-position and/or the 3-position or higher with respect to the olefin double bond. By itself, the term "alpha olefin" does not indicate the presence or absence of heteroatoms and/or the presence or absence of other carbon-carbon double bonds unless explicitly indicated. The terms "hydrocarbon alpha olefin" or "alpha olefin hydrocarbon" refer to alpha olefin compounds containing only hydrogen and carbon.

The term "linear alpha olefin" as used herein refers to a linear olefin having a double bond between the first and second carbon atom. The term "linear alpha olefin" by itself does not indicate the presence or absence of heteroatoms and/or the presence or absence of other carbon-carbon double bonds, unless explicitly indicated. The terms "linear hydrocarbon alpha olefin" or "linear alpha olefin hydrocarbon" refers to linear alpha olefin compounds containing only hydrogen and carbon.

The term "normal alpha olefin" whenever used in this specification and claims refers to a linear hydrocarbon mono-olefin having a double bond between the first and second carbon atom. It is noted that "normal alpha olefin" is not synonymous with "linear alpha olefin" as the term "linear alpha olefin" can include linear olefinic compounds having a double bond between the first and second carbon atoms and having heteroatoms and/or additional double bonds.

The term "cross-linked polyethylene (PE)" whenever used in this specification and claims refers to compounds comprising a first linear or branched hydrocarbon that has a covalent bond to a second linear or branched hydrocarbon and that are in the solid phase at standard conditions.

The term "micron" whenever used in this specification and claims refers to one micrometer (1 μm).

Disclosed are processes and systems for the deactivation of alkyl aluminum catalysts. The deactivation can be performed by adding water to an oligomerization reactor effluent. The addition of water simplifies downstream separations for recovery of the oligomer(s) from the deactivated catalyst compared to techniques which utilize sodium hydroxide for alkyl aluminum catalyst deactivation. The downstream separations can generally utilize filtration technology for recovery of the oligomer product from the deactivated catalyst. It has been found that the deactivation disclosed herein unexpectedly produces solids that act as a filter aid to reduce plugging of the filter.

Figure 2:
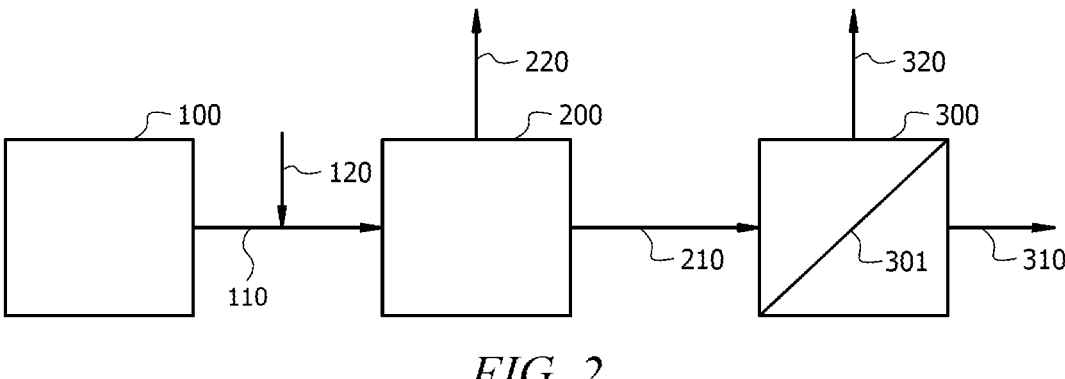
FIG. 2 is a schematic diagram of an alternative alkyl aluminum catalyst deactivation system and process as described herein.

FIG. 1 and FIG. 2 are schematic diagrams of alkyl aluminum catalyst deactivation systems and processes. In both FIG. 1 and FIG. 2, the system and process include an oligomerization reactor 100, a mixing vessel 200 having a first inlet fluidly coupled to an outlet of the oligomerization reactor 100, and a separator 300 having an inlet fluidly coupled to an outlet of the mixing vessel 200. A reactor effluent stream 110 is connected to an outlet of the oligomerization reactor 100 and to an inlet of the mixing vessel 200. The reactor effluent stream 110 is configured to allow flow of a reactor effluent from the oligomerization reactor 100 to the mixing vessel 200. A treated product stream 210 is connected to a first outlet of the mixing vessel 200 and to an inlet of the separator 300, and a vapor stream 220 is connected to a second outlet of the mixing vessel 200. The treated product stream 210 is configured to allow flow of a treated product from the mixing vessel 200 to the separator 300. The vapor stream 220 is configured to allow flow of gas phase components (e.g., unreacted olefin monomer) from the mixing vessel 200. In some aspects, the vapor stream 220 can be connected to a monomer recovery system or to an inlet of the oligomerization reactor 100, e.g., for recycle of the unreacted olefin monomer to the oligomerization reactor 100.

The processes and systems in FIG. 1 and FIG. 2 are different, in that, a water stream 120 is fluidly coupled to a second inlet of the mixing vessel 200 in FIG. 1 (with the reactor effluent stream 110 being fluidly coupled to the first inlet), while the water stream 120 is fluidly coupled to a first inlet of the mixing vessel 200 in FIG. 2 via connection to the reactor effluent stream 110 at a location in the reactor effluent stream 110 that is upstream of the mixing vessel 200 in FIG. 2. The water stream 120 is configured to allow a flow of water to combine with the oligomer product in the reactor effluent to form a treated product, either in the mixing vessel 200 as illustrated in FIG. 1 or in the reactor effluent stream 110 upstream of the mixing vessel 200 as illustrated in FIG. 2.

The discussion below can apply to the processes and systems in FIG. 1 and FIG. 2, except where differences are discussed relative to the location where water is combined with the reactor effluent via the water stream 120.

Oligomerization

The oligomerization reactor 100 is configured to contact an olefin monomer with an alkyl aluminum catalyst under oligomerization conditions to form an oligomer product that includes an oligomer produced by an oligomerization reaction.

In aspects, the olefin monomer can be fed to the oligomerization reactor 100 via a feed stream connected to an inlet of the oligomerization reactor 100. The olefin monomer can include one or more alpha olefins, one or more linear alpha olefins, one or more normal alpha olefins, or a combination thereof. Generally, the alpha olefin(s), linear alpha olefin(s), or normal alpha olefin(s) may be $C_2$ to $C_{30}$, $C_2$ to $C_{16}$, or $C_2$ to $C_{10}$ olefin(s), alpha olefin(s), linear alpha olefin(s), or normal alpha olefin(s). In an embodiment, the olefin monomer comprises, or consists essentially of, ethylene.

The oligomerization reactor 100 can be any suitable reactor or vessel suitable to contact the olefin monomer with the alkyl aluminum catalyst to form one or more oligomers via oligomerization (e.g., dimerization, trimerization) reactions. Non-limiting examples of a reactor or vessel can include a plug flow reactor, a continuous stirred tank reactor, or combinations thereof, including multiple reactors in series and/or in parallel.

The oligomer product is withdrawn (or is otherwise removed), from the oligomerization reactor 100 as a reactor effluent via the reactor effluent stream 110. In aspects, the oligomer product can include, in addition to the oligomer(s): the alkyl aluminum catalyst, unreacted olefin monomer, diluent, or combinations thereof. In several aspects, the oligomer product can also include a polymer (e.g., cross-linked polyethylene (PE)) that is insoluble in the oligomer produced by the oligomerization reaction. In several aspects, the polymer (e.g., cross-linked polyethylene (PE)) can be produced by the oligomerization reaction. In aspects, the polymer (e.g., cross-linked polyethylene (PE)) may be insoluble (not soluble) in the oligomer product. In several aspects, the oligomer product includes the polymer (e.g., cross-linked polyethylene (PE)) in a range of from about 0.01 to about 10 wt %; alternatively, from 0.1 to 1 wt %; or, alternatively, from 0.2 to 0.5 wt % based on a total weight of the oligomer product. In several aspects, the oligomer product includes less than 1 wt % of the polymer (e.g., cross-linked polyethylene (PE)) based on a total weight of the oligomer product, a range which includes those aspects where polymer is present in the oligomer product and those aspects where no polymer (e.g., cross-linked polyethylene (PE)) is produced by the oligomerization reaction, and thus, no polymer is included in the oligomer product.

In aspects, the oligomer produced by the oligomerization reaction can include one or more alpha olefin oligomers, one or more linear alpha olefin oligomers, one or more normal alpha olefin oligomers, or a combination thereof. In several aspects, the oligomer produced by the oligomerization reaction is an alpha olefin oligomer.

In several aspects, the diluent can include a $C_2$ to $C_{20}$ saturated hydrocarbon.

The contacting step performed in the oligomerization reactor 100 can be conducted at a variety of temperatures, pressures, and contact times. Contacting can generally include initial contact of the olefin monomer (e.g., one or more normal alpha olefins) with the alkyl aluminum catalyst and continued contact during oligomerization. For instance, the temperature at which the olefin monomer (e.g., one or more normal alpha olefins) and the alkyl aluminum catalyst are initially contacted can be the same as, or different from, the temperature at which the oligomer product is formed. As an illustrative example, in the contacting step, the olefin monomer (e.g., one or more normal alpha olefins) and the alkyl aluminum catalyst can be contacted initially at temperature T1 and, after this initial combining, the temperature can be changed to a temperature T2 to allow for the oligomerizing of the olefin monomer (e.g., one or more normal alpha olefins) form the oligomer product. Likewise, the pressure in the contacting step can be at pressure P1 for initial contact and P2 for oligomerizing the olefin monomer (e.g., one or more normal alpha olefins). The contact time can be referred to as the reaction time.

In aspects, the contacting step for oligomerization can be conducted at a minimum temperature of 50° C., 55° C., 60° C., 65° C., or 70° C.; or alternatively, at a maximum temperature of 220° C., 210° C., 200° C., 190° C., 180° C., 170° C., 160° C., 150° C., 140° C., 130° C., 125° C., 120° C., 120° C., 115° C., or 110° C. In aspects, the contacting step (for oligomerization) can be conducted at a temperature in a range from any minimum temperature disclosed herein to any maximum temperature disclosed herein. In some non-limiting embodiments, the contacting step can be conducted at temperature in a range from 50° C. to 220° C.; alternatively, from 70° C. to 220° C.; alternatively, from 50° C. to 200° C.; alternatively, from 60° C. to 190° C. These temperature ranges can also encompass circumstances where the contacting step can be conducted at a series of different temperatures, instead of at a single fixed temperature, falling within the respective temperature ranges.

In aspects, the contacting step for oligomerization can be conducted at a pressure in a range of from atmospheric pressure (0 psig or 0 MPag) to about 2500 psig (17.2 MPag); alternatively, from atmospheric to about 1600 psig (11.0 MPag); alternatively, from about 300 psig (2.0 MPag) to about 900 psig (6.2 MPag). In some embodiments, the contacting step can be conducted at sub-atmospheric pressures.

In aspects, the conversion of the olefin monomer (e.g., one or more normal alpha olefins) is described as "monomer conversion" to indicate that the percentage conversion, in weight percent or in mole percent, is based on the olefin monomer (e.g., one or more normal alpha olefins) and does not include non-monomer materials that can be present. In aspects, a minimum monomer conversion can be at least 10%, by weight percent or by mole percent. In another embodiment, the minimum monomer conversion can be at least 15%, at least 20%, at least 25%, at least 30%, at least 40%, or at least 50%, and these percentages can be weight percentages or mole percentages. In yet another embodiment, the maximum monomer conversion can be 90%, 85%, 80%, 75%, 70%, 65%, 60%, or 55%, and these percentages can be weight percentages or mole percentages. Generally, the monomer conversion can be in a range from any minimum monomer conversion disclosed herein to any maximum monomer conversion disclosed herein. Non-limiting ranges of monomer conversion, in weight or mole percentages, can include, but are not limited to, the following ranges: from 10% to 90%, from 10% to 85%, from 10% to 75%, from 15% to 90%, from 15% to 75%, from 10% to 60%, from 10% to 50%, from 15% to 50%, from 10% to 45%, from 15% to 45%, from 10% to 40%, or from 15% to 45%. Other monomer conversion ranges are readily apparent from this disclosure. In some embodiments, these monomer conversions can be achieved in a batch process, while in other embodiments, these monomer conversions can be achieved in a flow or continuous process, such as, for example, a single pass through a reactor (e.g., a fixed bed reactor).

The alkyl aluminum catalyst can be any alkyl aluminum-based oligomerization catalyst, such as a non-hydrolyzed alkyl aluminum compound. In an embodiment, the non-hydrolyzed alkyl aluminum compound may be a trialkyl aluminum compound. Generally, each alkyl group of any alkyl aluminum compound described herein, if there is more than one, may independently be a $C_2$ to $C_{100}$ alkyl group. In several aspects, each aluminum atom in the aluminum alkyl catalyst is connected to three alkyl groups, wherein each alkyl group includes at least two carbon atoms. In several aspects, each aluminum atom in the aluminum alkyl catalyst is connected to three alkyl groups, wherein each alkyl group includes at least two carbon atoms. In aspects, each alkyl group can independently include from 2 to 100; alternatively, from 2 to 90; alternatively, from 2 to 80; alternatively, from 2 to 70; alternatively, from 2 to 60; alternatively, from 2 to 50; alternatively, from 2 to 40; or alternatively, from 2 to 30 carbon atoms.

Exemplary trialkyl aluminum compounds may include but are not limited to, trimethyl aluminum (TMA), triethyl aluminum (TEA), tripropyl aluminum, tri-n-butyl aluminum, or tri-isobutyl aluminum, or mixtures thereof. In various embodiments, the trialkyl aluminum compound may be triethyl aluminum.

In several aspects, the aluminum alkyl compound may be a mixture of a trialkyl aluminum compound and an alkyl aluminum halide. Generally, the trialkyl aluminum compound of the mixture may be any trialkyl aluminum compound described herein.

In aspects, no aluminum halide is present in the alkyl aluminum catalyst. In additional or alternative aspects, no aluminum alkoxide compound is present in the alkyl aluminum catalyst.

Combining Water with the Oligomer Product

The reactor effluent in reactor effluent stream 110 can include the oligomer product (e.g., the oligomer(s), the alkyl aluminum catalyst, unreacted olefin monomer, diluent, polymer, or combinations thereof). In aspects, the reactor effluent contains no significant amount of water which would deactivate the alkyl aluminum catalyst. The processes and systems disclosed herein combine water with the reactor effluent in an amount effective to deactivate the alkyl aluminum catalyst. To accomplish water addition to the oligomer product, the water stream 120 is connected to an inlet of the mixing vessel 200 in FIG. 1, while the water stream 120 is connected to the reactor effluent stream 110 in FIG. 2. The water stream 120 is configured to allow a flow of water to combine with the reactor effluent to form the treated product, either in the reactor effluent stream 110 as illustrated in FIG. 2, or in the mixing vessel 200 as illustrated in FIG. 1.

When combined with the reactor effluent, the water contacts the alkyl aluminum catalyst to initiate a hydrolysis reaction with aluminum atoms in the catalyst that deactivates the alkyl aluminum catalyst. In several aspects, deactivation of the alkyl aluminum catalyst includes its conversion into aluminum-containing solids that are not soluble (insoluble) in any of the components of the oligomer product (and thus insoluble in the treated product produced by combination of water with the reactor effluent). In several aspects, the aluminum-containing solids comprise aluminum atoms bonded only to oxygen atoms (e.g., aluminum oxides, aluminum hydroxides, or a combination thereof), aluminum atoms bonded to an alkyl group and at least one oxygen atom, or both aluminum atoms bonded only to oxygen atoms and aluminum atoms bonded to an alkyl group and at least one oxygen atom. In aspects, the aluminum-containing solids are inert under the conditions used in the processes and systems described herein. In aspects, the aluminum-containing solids include aluminum atoms bound to two or three oxygen atoms. In some aspects, the oxygen atom that is bonded to an aluminum atom may be bound to another aluminum atom. After treatment, some aspects contemplate that some aluminum atoms are still bound to at least one alkyl group because it has been found that two of the three alkyl groups on an aluminum alkyl compound react rather quickly with water, while the third alkyl group appears to react more slowly with water than the first two. In some aspects, the aluminum containing solids can contain up to about 80% aluminum atoms that have no bond to an alkyl group and up to about 20% aluminum atoms that are each bonded to one alkyl group.

In aspects, the combining step for catalyst deactivation can be conducted at a minimum temperature of 50° C., 60° C., 65° C., or 70° C.; additionally or alternatively, at a maximum temperature of 130° C., 125° C., 120° C., 115° C., 110° C., 105° C., 100° C., 95° C., or 90° C. In aspects, the combining step can be conducted at any temperature between any minimum temperature and any maximum temperature described herein for the combining step. In some non-limiting embodiments, the combining step can be conducted at temperature in a range from 50° C. to 130° C.; alternatively, from 70° C. to 130° C.; alternatively, from 50° C. to 125° C.; alternatively, from 60° C. to 130° C.; alternatively, from 65° C. to 120° C.; alternatively, from 70° C. to 125° C.; or alternatively, from 70° C. to 120° C. In other non-limiting embodiments, the combining step for catalyst deactivation can be conducted at a temperature in a range from 75° C. to 115° C., from 80° C. to 115° C., from 80° C. to 110° C., or from 85° C. to 110° C. These temperature ranges can also encompass circumstances where the combining step can be conducted at a series of different temperatures, instead of at a single fixed temperature, falling within the respective temperature ranges.

Combination of water with the reactor effluent forms the treated product. In FIG. 1, the treated product is formed in the mixing vessel 200; and in FIG. 2, the treated product is formed in the portion of the reactor effluent stream 110 that is between the entry point of water stream 120 and the mixing vessel 200. The treated product in the mixing vessel 200 and in the treated product stream 210 can include the oligomer(s), diluent, polymer, the aluminum-containing solids, or combinations thereof (since an additional function of the mixing vessel 200 is to separate the unreacted monomer from the rest of the components of the reactor effluent). In aspects, the treated product in the mixing vessel 200 and in the treated product stream 210 can include minor amounts of unreacted olefin monomer due to less than 100% efficient separation of the unreacted olefin monomer. In aspects of the process and system in FIG. 2, the treated product in the portion of the reactor effluent stream 110 that is between the water stream 120 and the mixing vessel 200 can additionally include unreacted olefin monomer that is present in the reactor effluent prior to removal of the unreacted olefin monomer from the other components in the reactor effluent in the mixing vessel 200.

In some aspects, the treated product can include unreacted water; alternatively, the water is added in an amount such that all water is consumed in reaction with the alkyl aluminum catalyst. In aspects were unreacted water is present, the unreacted water may adsorb onto the aluminum solids present in the treated product.

In aspects, water is combined with the oligomer product in a range of from 0.1 wt % to about 1 wt %; alternatively, from 0.1 wt % to 0.8 wt %; alternatively, from 0.2 wt % to 0.7 wt %; alternatively, from 0.4 wt % to 0.7 wt %; alternatively, about 0.2, 0.3, 0.4, 0.5, 0.6, or 0.7 wt % based on a total weight of the oligomer in the oligomer product.

In aspects, a mole ratio of the water to the alkyl aluminum catalyst can be in a range of from about 5:1 to about 15:1; alternatively, 6:1 to 14:1; alternatively, 7:1 to 13:1; alternatively, 8:1 to 12:1; alternatively, 9:1 to 10:1, based on a number of moles of the water that are combined with the oligomer product and a number of moles of the alkyl aluminum catalyst in the oligomer product. In aspects, water is combined with the oligomer product in a range of from 10 wt % to 20 wt %; alternatively, in a range of from 12 wt % to 18 wt %; alternatively, about 16 wt % based on a total weight of the alkyl aluminum catalyst in the oligomer product.

Mixing Vessel

The mixing vessel 200 can be any vessel or combination of vessels configured to mix the reactor effluent and water to from the treated product, e.g., with a stirring apparatus or an agitation apparatus. In aspects, the mixing vessel 200 simultaneously separates the unreacted olefin monomer in a gas phase from the liquid and solid phase components of the reactor effluent and water that mix to form the treated product in the mixing vessel 200.

In several aspects, the treated product can be mixed in the mixing vessel 200 for a mixing time in a range of from about 0.1 to about 30 hours; alternatively, from 0.2 to 10 hours; alternatively, from 0.3 to 3 hours; alternatively, from 0.3 to 1.5 hours. In several aspects, the treated product can be mixed at temperature in a range from 10° C. to 140° C.; alternatively, from 20° C. to 120° C.; alternatively, from 80° C. to 100° C.; alternatively, at ambient temperature.

The mixing vessel 200 has a first outlet that is connected to the treated product stream 210 that is configured to allow flow of the treated product out of the mixing vessel 200. The mixing vessel 200 has a second outlet that is connected to the vapor stream 220 that is configured to allow the unreacted olefin monomer to flow out of the mixing vessel 200 in a gas phase. The unreacted olefin monomer may flow out of the mixing vessel 200 before the treated product has been mixed, while the treated product is being mixed, after the treated product has been mixed, or a combination thereof. In several aspects, unreacted olefin monomer may flow out of the mixing vessel 200 with no mixing of the treated product in the mixing vessel 200. In several aspects, the unreacted olefin monomer is separated from the oligomer product within the mixing vessel 200. In several aspects, the unreacted olefin monomer is separated from the treated product within the mixing vessel 200.

It will be appreciated by the skilled artisan that the present disclosure contemplates that sodium hydroxide is not utilized for catalyst deactivation. That is, the process and system have no sodium hydroxide source configured to add sodium hydroxide in an amount that would cause the aluminum-containing solids to dissolve in the treated product. Sodium hydroxide is not added to the reactor effluent, the oligomer product, or the treated product in an amount that would cause the aluminum-containing solids to dissolve in the resulting mixture. Further, sodium hydroxide is not added to the reactor effluent, the oligomer product, or the treated product in an amount that would cause the aluminum-containing solids to dissolve in any water present in the resulting mixture. In aspects, sodium hydroxide (e.g., as an aqueous solution or a solid) is not combined with the reactor effluent, sodium hydroxide is not combined with the oligomer product, and sodium hydroxide is not combined with the treated product.

Separation of Aluminum-Containing Solids by Filtration

The treated product stream 210 can be connected to an inlet of a separator 300 comprising at least one filter 301. The separator 300 can be embodied as a housing having one or more filters 301 contained therein. The filter 301 can also be referred to as a filter element or filtration element that is configured to separate molecules and particles based on the size of the molecules and particles relative to a pore size of pores in the filter 301. Molecules and particles smaller than the pore size of the filter 301 pass through the filter 301 as a permeate to a permeate side of the separator 300, and molecules and particles larger than the pore size of the filter 301 are retained as retentate on a retentate side of the separator 300.

In aspects, the pores of the filter 301 have a pore size (e.g., an average pore size) in a range of from about 1 micron to about 100 microns; alternatively, 1 to 30 microns; alternatively, 1 to 25 microns; alternatively, 1 to 20 microns; alternatively, 10 to 30 microns; alternatively, 10 to 25 microns; alternatively, 10 to 20 microns; alternatively, 20 to 25 microns.

In aspects, the filter 301 can be made of a ceramic material, a metal (e.g., stainless steel) material, a polymeric material, or combinations thereof. In several aspects, the filter 301 can be a polymeric material that includes cellulose acetate, cellulose nitrate, polyamide, polycarbonate, polyethersulphone, polytetrafluoroethylene, or combinations thereof. In aspects, the filter 301 can be a membrane filter.

Commercial examples of the filter 301 can include a clarifying filter, such as a rotary drum filter or a pressure leaf filter. In commercial operation, a filter cake can form on the retentate side of the filter 301, and there may be a need to break up and/or remove the filter cake (or at least portions of the filter cake). The filter 301 can have a mechanism for "blowback" of the filter cake, such as a pressurized stream of inert hydrocarbon that flows from the permeate side of the filter 301 to the retentate side of the filter 301, dislodging and breaking up portions of the filter cake for removal via the retentate stream 320. Blowback can be initiated upon a differential pressure between the permeate side and the retentate side reaching a hydraulic threshold.

The separator 300 can have a permeate outlet connected to the permeate stream 310 and a retentate outlet connected to the retentate stream 320. The permeate stream 310 is configured to allow permeate to flow from the separator 300, and the retentate stream 320 is configured to allow retentate to flow from the separator 300. In aspects, the permeate in the permeate stream 310 includes the oligomer(s), diluent, unreacted water, or combinations thereof. In aspects, the retentate in the retentate stream 320 can include the aluminum-containing solids, and in some aspects, also the polymer (e.g., cross-linked polyethylene (PE)).

In aspects, some of the aluminum-containing solids can accumulate on the retentate side of the filter 301. The accumulation of the aluminum-containing solids can function as a filter aid, in that, the aluminum-containing solids can loosely pack as a layer on the retentate side of the filter 301 to prevent, when polymer is present in the treated product, the polymer from packing or depositing as a layer on the retentate side of the filter 301. Polymer deposit on the retentate side of the filter 301 can reduce permeate flow through the filter 301, and the aluminum-containing solids prevent the polymer from depositing on the retentate side of the filter 301.

In aspects, the filter 301 of the separator 300 removes from about 95 wt % to about 99 wt %; alternatively, from about 96 wt % to about 99 wt %; alternatively, from about 97 wt % to about 99 wt %; alternatively, from about 98 wt % to about 99 wt % of the aluminum that is contained in the treated product stream 210 (based on a total weight of the treated product stream 210), such that the permeate stream 310 has less than 50, 40, 30, or 20 ppmw aluminum based on a total weight of the permeate stream 310.

Figure 3:
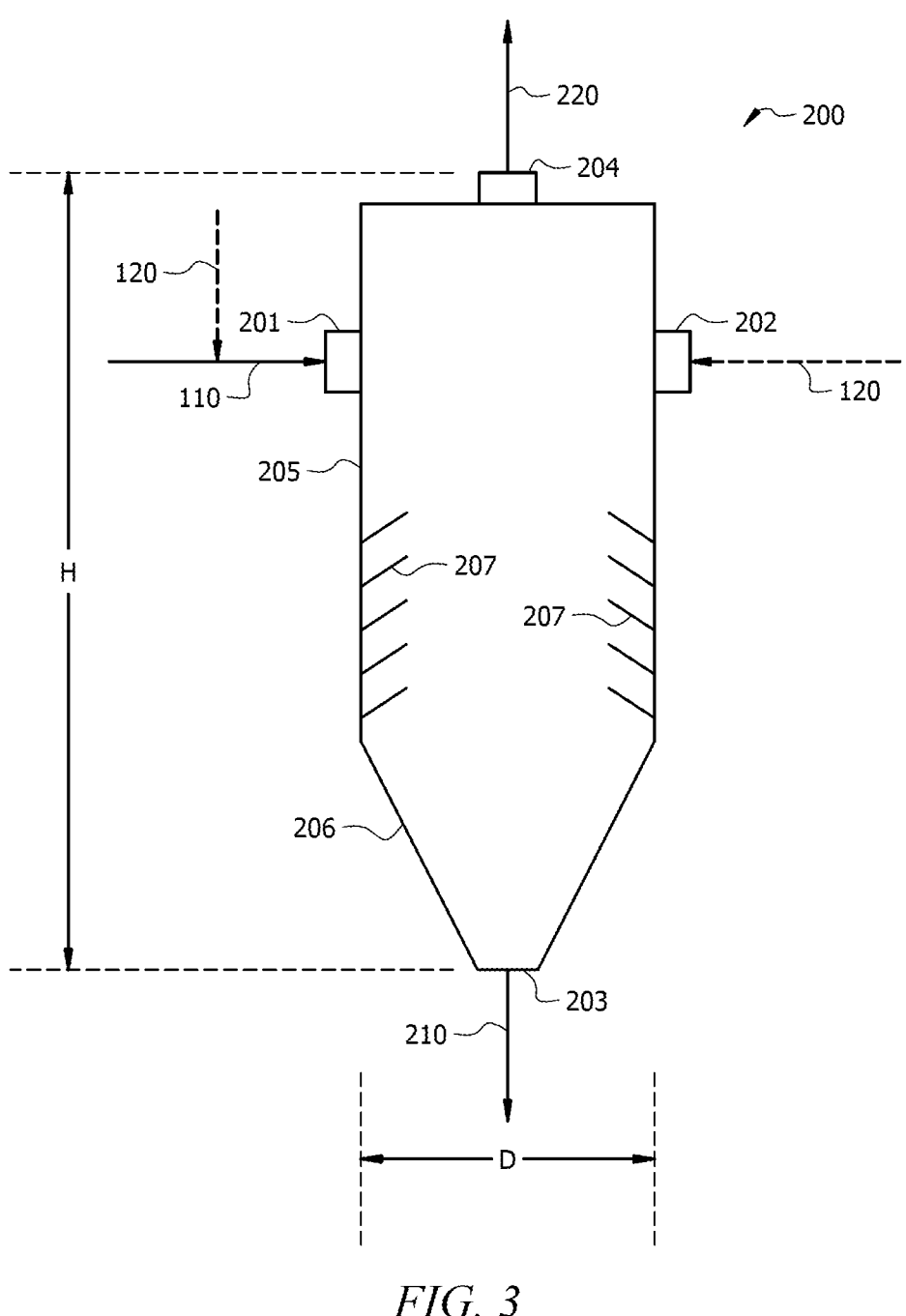
FIG. 3 is a cross sectional view of an embodiment of the mixing vessel in FIGS. 1 and 2.

FIG. 3 is a cross sectional view of an embodiment of the mixing vessel 200 in FIGS. 1 and 2. The mixing vessel 200 includes a first inlet 201, an optional second inlet 202, a first outlet 203, and a second outlet 204. The first inlet 201 connects to the reactor effluent stream 110 and is configured to receive the oligomer product in the reactor effluent (when water stream 120 is connected to the second inlet 202) or the treated product (when water stream 120 is connected to the reactor effluent stream 120 upstream of the first inlet 201) from the reactor effluent stream 110. The second inlet 202 is utilized for the process and system in FIG. 1 where the water stream 120 is connected to the mixing vessel 200. The first outlet 203 is connected to the treated product stream 210. The second outlet 204 is connected to the vapor stream 220. The mixing vessel 200 is configured to separate the unreacted olefin monomer from the treated product in the mixing vessel 200 and to recover the unreacted olefin monomer via the second outlet 204.

The mixing vessel 200 can include a mixing assembly configured to mix the contents of the mixing vessel 200, e.g., a stirring apparatus or an agitation apparatus. In other aspects, mixing can occur by force of the flow of the components into the mixing vessel 200 as the components travel from the top of the vessel 200 to the bottom of the vessel 200. In some aspects, baffles 207 can enhance mixing as components of the reactor effluent/treated product flow from top to bottom of the mixing vessel 200.

The mixing vessel 200 can have a cylindrical portion 205 and a conical portion 206 below the cylindrical portion 205. In several aspects, the treated product can flow vertically downward through the cylindrical portion 205 of the mixing vessel 200 into the conical portion 206, and then the treated product can continue to flow vertically downward through the conical portion 206 to the outlet 203.

The mixing vessel 200 can have a height H and a diameter D. In several aspects, a ratio of height to diameter is in a range of from about 1:1 to about 10:1; alternatively, from 2:1 to 8:1; alternatively, from 3:1 to 6:1.

An example of a process disclosed herein includes combining water with an oligomer product comprising an oligomer and an alkyl aluminum catalyst to form a treated product comprising the oligomer and aluminum-containing solids; and separating, by a filter, the treated product into a permeate stream comprising the oligomer and a retentate stream comprising the aluminum-containing solids. The process can additionally include, after combining and before separating, mixing the treated product. In aspects where the oligomer product includes unreacted olefin monomer and the treated product further comprises the unreacted olefin monomer, the process can additionally include separating the unreacted olefin monomer from the oligomer product or the treated product. In aspects of the process, water is combined with the oligomer product upstream of the mixing vessel or in the mixing vessel. The process can also include contacting an olefin monomer with an alkyl aluminum catalyst under oligomerization conditions to form an oligomer product in an oligomerization reactor, and withdrawing the oligomer product from an oligomerization reactor. Any of these process steps can be performed with any component, aspects, condition disclosed herein.

EXAMPLES

The subject matter of the present disclosure having been generally described, the following examples are given as particular aspects of the disclosure and to demonstrate the practice and advantages thereof. It is understood that the examples are given by way of illustration and are not intended to limit the specification or the claims to follow in any manner.

Example 1

A mixture simulating an oligomer product was prepared and treated to form a treated product. The treated product was then filtered, and results are reported in FIG. 4.

The oligomer product was prepared by combining 212.5 g of $C_{16}$ and $C_{18}$ hydrocarbon oligomers and 24.5 g of a mixture of crosslinked polyethylene (PE) and $C_{30+}$ oligomers. The oligomer product was heated and stirred in a 500 mL round bottomed flask at 90° C.

Separately and under an inert atmosphere in a dry box, 3.1 g of tri-n-octyl aluminum (TNOA, the alkyl aluminum catalyst in this Example 1) and 10.0 g of the $C_{16}$ and $C_{18}$ hydrocarbon oligomers were combined in an addition funnel equipped with stopcock having a pressure equalization tube. The addition funnel was removed from the dry box and connected to the round bottomed flask which was subsequently flushed with dry nitrogen. The contents of the addition funnel were then added into the round bottomed flask such that the simulated oligomer product contained alkyl aluminum catalyst (the TNOA). Distilled water (0.5 g, 0.2 wt % water based on the oligomer mass) was added to the round bottomed flask via syringe to produce a treated product. Hydrolysis of the TNOA was evident by the immediate formation of white solids.

Figure 4:
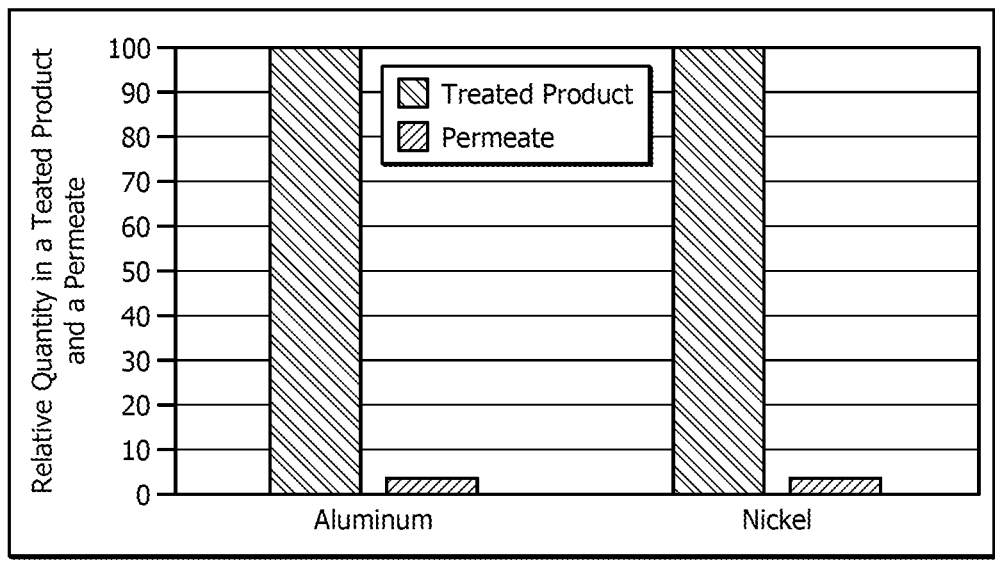
FIG. 4 is a graph of the relative quantity of aluminum and nickel in a treated product and in a permeate obtained by filtration of the treated product through a filter having pore size of 20-25 microns.

The treated product was stirred for 15 minutes, and 1 g of a tetradecene solution of nickel octanoate (2.1 wt % Ni in the solution) was added to provide 80 ppmw Ni in the treated product. The treated product was stirred another 10 minutes and then vacuum filtered through 42.5 mm diameter Whatman 4 paper (20-25 microns) on a Buchner Funnel. The permeate was analyzed by Inductively Coupled Plasma Spectroscopy (ICP). The ICP analysis found that the permeate contained only 1.5 wt % of the amount of aluminum in the treated product and only 2 wt % of the amount of nickel in the treated product. The relative quantity of aluminum and nickel in the treated product and permeate is displayed in FIG. 4. As can be seen, the relative quantities in FIG. 4 illustrate that 98.5 wt % of the aluminum and 98.0 wt % of the nickel were removed by filtration.

No sodium hydroxide was added to any mixture in Example 1. Thus, Example 1 demonstrates treatment of an oligomer product to remove alkyl aluminum catalyst without use of sodium hydroxide.

Example 1 demonstrates that treatment of an oligomer product containing an alkyl aluminum catalyst with water hydrolyzes the aluminum atoms, and the hydrolyzed aluminum atoms then form aluminum-containing solids that are insoluble in the treated product and can be filtered from the treated product to recover the valuable oligomers in the permeate.

Nickel was added to the oligomer product in Example 1 to demonstrate the additional ability to remove nickel-containing solids in the same filtration step that removes aluminum-containing solids. That is, in aspects where nickel-containing solids are present in the oligomer product, the disclosed hydrolysis of aluminum atoms in an alkyl aluminum catalyst to form aluminum-containing solids creates a complementary need to filter an additional amount solids from the oligomer product.

Example 2

Mixtures simulating an oligomer product and treated products were prepared to compare filtration times. The oligomer product was prepared by combining 22 g C30+ oligomers with 0.1 g of crosslinked polyethylene (PE) (0.5 wt % PE based on the total weight of the C30+ oligomers). A first treated product was prepared by combining 22 g C30+ oligomers with 0.1 g of crosslinked polyethylene (PE) (0.5 wt % PE based on the total weight of the C30+ oligomers), and then adding 2 grams of aluminum hydroxide $(Al(OH)_3)$. A second treated product was prepared by combining 22 g C30+ oligomers with 0.1 g of crosslinked polyethylene (PE) (0.5 wt % PE based on the total weight of the C30+ oligomers), and then adding 2 grams of aluminum oxide $(Al_2O_3)$.

Figure 5:
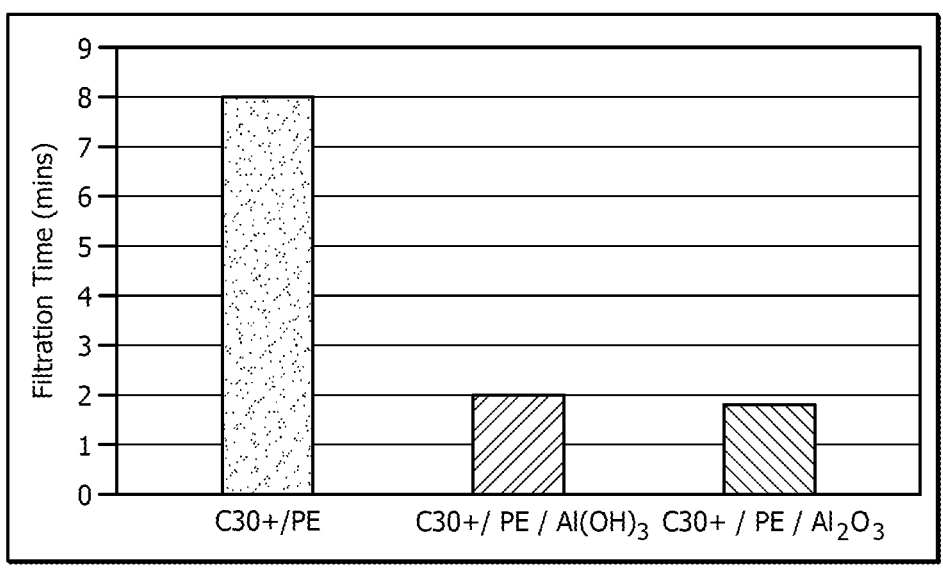
FIG. 5 displays a comparison of the filtration times through a filter having pore size of 20-25 microns for i) a $C_{30+}$ oligomer product containing particles of polyethylene and no aluminum-containing solids, ii) a $C_{30+}$ oligomer product containing particles of polyethylene and aluminum hydroxide solids, and iii) a $C_{30+}$ oligomer product containing particles of polyethylene and aluminum oxide solids.

Each mixture was filtered at 80-90° C. as described in Example 1 (through 42.5 mm diameter Whatman 4 paper (20-25 microns) on a Büchner Funnel) while maintaining the temperature of the funnel above the melting point of the $C_{30+}$ oligomers. Times required for the entire filtrate to pass through the filter were recorded, as displayed in FIG. 5. While attempting to filter the oligomer product, the filter became plugged quickly and filtration was incomplete and stopped after 8 minutes. Filtration times for the treated products were approximately 2.0 minutes for first treated product and 1.7 minutes for the second treated product.

Example 2 demonstrates that aluminum-containing solids in a treated product that also contains polyethylene particles functions as a filter aid to prevent the polyethylene particles from plugging the filter. The ability of the aluminum-containing solids to function as a filter aid was not expected.

Additional Disclosure

Accordingly, the scope of protection is not limited by the description set out above but is only limited by the claims which follow, that scope including all equivalents of the subject matter of the claims. Each and every claim is incorporated into the specification as part of the disclosure. Thus, the claims are a further description and are an addition to the detailed description. The disclosures of all patents, patent applications, and publications cited herein are hereby incorporated by reference.

Aspect 1. A process comprising: combining water with an oligomer product comprising an oligomer and an alkyl aluminum catalyst to form a treated product comprising the oligomer and aluminum-containing solids; and separating, by a filter, the treated product into a permeate stream comprising the oligomer and a retentate stream comprising the aluminum-containing solids.

Aspect 2. The process of Aspect 1, wherein the oligomer product further comprises a polymer, wherein the treated product further comprises the polymer, wherein the retentate stream further comprises the polymer.

Aspect 3. The process of Aspect 2, wherein an amount of the polymer in the oligomer product is less than 1 wt % based on a total weight of the oligomer product.

Aspect 4. The process of any one of Aspects 1 to 3, wherein the aluminum-containing solids are not soluble in the treated product.

Aspect 5. The process of any one of Aspects 1 to 4, wherein water is combined with the oligomer product in a range of from 0.1 wt % to about 1 wt % based on a total weight of the oligomer in the oligomer product.

Aspect 6. The process of any one of Aspects 1 to 5, wherein a mole ratio of the water to the alkyl aluminum catalyst is from about 5:1 to about 15:1 based on a number of moles of the water that are combined with the oligomer product and a number of moles of the alkyl aluminum catalyst in the oligomer product.

Aspect 7. The process of any one of Aspects 1 to 6, wherein the filter has a pore size in a range of from about 1 micron to about 30 microns.

Aspect 8. The process of any one of Aspects 1 to 7, wherein the aluminum-containing solids comprise aluminum atoms bonded only to oxygen atoms, aluminum atoms bonded to an alkyl group and at least one oxygen atom, or both aluminum atoms bonded only to oxygen atoms and aluminum atoms bonded to an alkyl group and at least one oxygen atom.

Aspect 9. The process of any one of Aspects 1 to 8, further comprising: after combining and before separating, mixing the treated product.

Aspect 10. The process of any one of Aspects 1 to 9, wherein the oligomer product further comprises unreacted olefin monomer, wherein the treated product further comprises the unreacted olefin monomer, the process further comprising: separating the unreacted olefin monomer from the oligomer product or the treated product.

Aspect 11. The process of any one of Aspects 1 to 10, wherein the water is combined with the oligomer product upstream of a mixing vessel or in the mixing vessel.

Aspect 12. The process of any one of Aspects 1 to 11, further comprising: withdrawing the oligomer product from an oligomerization reactor.

Aspect 13A. The process of any one of Aspects 1 to 12, wherein each aluminum atom in the alkyl aluminum catalyst is connected to three alkyl groups, wherein each alkyl group has from 2 to 100 carbon atoms.

Aspect 13B. The process of any one of Aspects 1 to 13A, wherein the permeate stream has less than 50 ppmw aluminum based on a total weight of the permeate stream.

Aspect 14. An alkyl aluminum catalyst deactivation system comprising: an oligomerization reactor configured to contact an olefin monomer in a presence of an alkyl aluminum catalyst to form an oligomer product comprising an oligomer and the alkyl aluminum catalyst; a mixing vessel having a first inlet fluidly coupled to an outlet of the oligomerization reactor; a water stream fluidly coupled to the first inlet of the mixing vessel or to a second inlet of the mixing vessel, wherein the water stream comprises water and is configured to combine the water with the oligomer product to deactivate the alkyl aluminum catalyst, wherein the water is combined with the oligomer product at a location that is i) upstream of the first inlet of the mixing vessel or ii) in the mixing vessel; and a separator having an inlet coupled to an outlet of the mixing vessel, wherein the separator comprises a filter and is configured to filter a treated product received from the mixing vessel into a permeate stream and a retentate stream, wherein the treated product comprises the oligomer and aluminum-containing solids, wherein the permeate stream comprises the oligomer, wherein the retentate stream comprises the aluminum-containing solids.

Aspect 15. The alkyl aluminum catalyst deactivation system of Aspect 14, wherein the water stream is configured to combine the water with the oligomer product upstream of the first inlet of the mixing vessel to form the treated product, wherein the first inlet of the mixing vessel is configured to receive the treated product.

Aspect 16. The alkyl aluminum catalyst deactivation system of any one of Aspect 14 to 15, wherein the water stream is configured to combine the water with the oligomer product in the mixing vessel to form the treated product in the mixing vessel, wherein the first inlet of the mixing vessel is configured to receive the oligomer product.

Aspect 17. The alkyl aluminum catalyst deactivation system of any one of Aspects 14 to 16, wherein the filter has a pore size in a range of from about 1 micron to about 30 microns.

Aspect 18. The alkyl aluminum catalyst deactivation system of any one of Aspects 14 to 17, having no sodium hydroxide source configured to add sodium hydroxide in an amount that would cause the aluminum-containing solids to dissolve in the treated product.

Aspect 19. The alkyl aluminum catalyst deactivation system of any one of Aspects 14 to 18, wherein the mixing vessel has a second outlet, wherein the oligomer product further comprises an unreacted olefin monomer, wherein the mixing vessel is configured to separate the unreacted olefin monomer from the treated product and to recover the unreacted olefin monomer via the second outlet.

Aspect 20. The alkyl aluminum catalyst deactivation system of any one of Aspects 14 to 19, wherein the oligomer product further comprises a polymer, wherein the treated product further comprises the polymer, wherein the retentate stream further comprises the polymer.

Although the present disclosure and its advantages have been described in detail, various changes, substitutions, and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:
1. A process comprising:
   combining water with an oligomer product comprising an oligomer and an alkyl aluminum catalyst to form a treated product comprising the oligomer and aluminum-containing solids; and separating, by a filter, the treated product into a permeate stream comprising the oligomer and a retentate stream comprising the aluminum-containing solids, wherein a mole ratio of the water to the alkyl aluminum catalyst is from about 5:1 to about 15:1 based on a number of moles of the water that are combined with the oligomer product and a number of moles of the alkyl aluminum catalyst in the oligomer product.

2. The process of claim 1, wherein the oligomer product further comprises a polymer, wherein the treated product further comprises the polymer, wherein the retentate stream further comprises the polymer.

3. The process of claim 2, wherein an amount of the polymer in the oligomer product is less than 1 wt % based on a total weight of the oligomer product.

4. The process of claim 1, wherein the aluminum-containing solids are not soluble in the treated product.

5. The process of claim 1, wherein the water is combined with the oligomer product in a range of from 0.1 wt % to about 1 wt % based on a total weight of the oligomer in the oligomer product.

6. The process of claim 1, wherein the filter has a pore size in a range of from about 1 micron to about 30 microns.

7. The process of claim 1, wherein the aluminum-containing solids comprise aluminum atoms bonded only to oxygen atoms, aluminum atoms bonded to an alkyl group and at least one oxygen atom, or both aluminum atoms bonded only to oxygen atoms and aluminum atoms bonded to an alkyl group and at least one oxygen atom.

8. The process of claim 1, further comprising:

after combining and before separating, mixing the treated product.

9. The process of claim 8, wherein the oligomer product further comprises unreacted olefin monomer, wherein the treated product further comprises the unreacted olefin monomer, the process further comprising:

separating the unreacted olefin monomer from the oligomer product or the treated product.

10. The process of claim 1, wherein the permeate stream has less than 50 ppmw aluminum based on a total weight of the permeate stream.

11. The process of claim 1, wherein each aluminum atom in the alkyl aluminum catalyst is connected to three alkyl groups, wherein each alkyl group has from 2 to 100 carbon atoms.

12. An alkyl aluminum catalyst deactivation system comprising:

an oligomerization reactor configured to contact an olefin monomer in a presence of an alkyl aluminum catalyst to form an oligomer product comprising an oligomer and the alkyl aluminum catalyst;

a mixing vessel having a first inlet fluidly coupled to an outlet of the oligomerization reactor;

a water stream fluidly coupled to the first inlet of the mixing vessel or to a second inlet of the mixing vessel, wherein the water stream comprises water and is configured to combine the water with the oligomer product to deactivate the alkyl aluminum catalyst, wherein the water is combined with the oligomer product at a location that is i) upstream of the first inlet of the mixing vessel or ii) in the mixing vessel; and a separator having an inlet coupled to an outlet of the mixing vessel, wherein the separator comprises a filter and is configured to filter a treated product received from the mixing vessel into a permeate stream and a retentate stream, wherein the treated product comprises the oligomer and aluminum-containing solids, wherein the permeate stream comprises the oligomer, wherein the retentate stream comprises the aluminum-containing solids, wherein a mole ratio of the water to the alkyl aluminum catalyst is from about 5:1 to about 15:1 based on a number of moles of the water that are combined with the oligomer product and a number of moles of the alkyl aluminum catalyst in the oligomer product.

13. The alkyl aluminum catalyst deactivation system of claim 12, wherein the water stream is configured to combine the water with the oligomer product upstream of the first inlet of the mixing vessel to form the treated product, wherein the first inlet of the mixing vessel is configured to receive the treated product.

14. The alkyl aluminum catalyst deactivation system of claim 12, wherein the water stream is configured to combine the water with the oligomer product in the mixing vessel to form the treated product in the mixing vessel, wherein the first inlet of the mixing vessel is configured to receive the oligomer product.

15. The alkyl aluminum catalyst deactivation system of claim 12, wherein the filter has a pore size in a range of from about 1 micron to about 30 microns.

16. The alkyl aluminum catalyst deactivation system of claim 12, having no sodium hydroxide source configured to add sodium hydroxide in an amount that would cause the aluminum-containing solids to dissolve in the treated product.

17. The alkyl aluminum catalyst deactivation system of claim 12, wherein the mixing vessel has a second outlet, wherein the oligomer product further comprises an unreacted olefin monomer, wherein the mixing vessel is configured to separate the unreacted olefin monomer from the treated product and to recover the unreacted olefin monomer via the second outlet.

18. The alkyl aluminum catalyst deactivation system of claim 12, wherein the oligomer product further comprises a polymer, wherein the treated product further comprises the polymer, wherein the retentate stream further comprises the polymer.

* * * * *